United States Patent [19]
Sarkisian et al.

[11] Patent Number: 5,658,347
[45] Date of Patent: Aug. 19, 1997

[54] ACETABULAR CUP WITH KEEL

[76] Inventors: James S. Sarkisian, 8415 Grant St., La Mesa, Calif. 92041; Clarence F. Batchelder, 17087 Skyline Truck Trail, Jamul, Calif. 92035-9712

[21] Appl. No.: 640,113

[22] Filed: Apr. 30, 1996

Related U.S. Application Data

[63] Continuation of Ser. No. 232,689, Apr. 25, 1994, abandoned.
[51] Int. Cl.$^6$ ..................................................... A61F 2/34
[52] U.S. Cl. .................................. 623/22; 623/18; 623/19
[58] Field of Search ............................ 623/16, 18, 19, 623/22, 23

[56] References Cited

U.S. PATENT DOCUMENTS

| | | |
|---|---|---|
| 4,085,466 | 4/1978 | Goodfellow . |
| 4,224,699 | 9/1980 | Weber . |
| 4,229,841 | 10/1980 | Youm . |
| 4,261,064 | 4/1981 | Helfet . |
| 4,301,553 | 11/1981 | Noiles . |
| 4,349,992 | 9/1982 | Agee . |
| 4,790,851 | 12/1988 | Suire . |
| 4,944,758 | 7/1990 | Bekki . |
| 4,959,071 | 9/1990 | Brown . |
| 4,976,740 | 12/1990 | Kleiner . |
| 5,007,932 | 4/1991 | Bekki . |
| 5,047,057 | 9/1991 | Lawes . |
| 5,047,059 | 9/1991 | Saffar . |
| 5,071,438 | 12/1991 | Jones . |
| 5,133,758 | 7/1992 | Hollister . |
| 5,147,386 | 9/1992 | Carignan . |
| 5,171,286 | 12/1992 | Lawes et al. ................ 623/22 |
| 5,192,329 | 3/1993 | Christie et al. ............. 623/22 |
| 5,314,488 | 5/1994 | Hayashi et al. ............. 623/22 |
| 5,443,519 | 8/1995 | Averill et al. ............... 623/22 |

FOREIGN PATENT DOCUMENTS

| | | | |
|---|---|---|---|
| 0241361 | 10/1987 | European Pat. Off. ............ 623/22 |
| 0331625 | 9/1989 | European Pat. Off. ............ 623/22 |
| 2578162 | 9/1986 | France .......................... 623/22 |
| 28 45 231 | 5/1979 | Germany . |
| 3620460 | 10/1987 | Germany ......................... 623/22 |
| 0561056 | 4/1975 | Switzerland ..................... 623/22 |
| 602 171 | 3/1978 | U.S.S.R. . |

OTHER PUBLICATIONS

*Porous Hip System: Surgical Technique*, William H. Harris, M.D., The Total System. Aug. 1984.
*At the Dawning of a New Era in Prosthetic Joint Replacement*, The Total System, Brochure.
*Total Hip Articular Replacement by Internal Eccentric Shells—The Tharies Technique for Surface Replacement*, Harlan C. Amstutz, M.D., and Ian C. Clark, Phd, Surgical Technique.

*Primary Examiner*—David Isabella
*Attorney, Agent, or Firm*—Brown, Martin, Haller & McClain

[57] ABSTRACT

A cup for reconstruction of an acetabulum in a pelvis, and a method for installing the apparatus. The cup is generally ellipsoidal in shape, with a rigid keel extending from the convex surface of the cup at a given angle. An ellipsoidal concave cavity is formed in the pelvis, and a stabilization channel is formed into the pelvis, at an angle which is close to, but slightly less than the angle on the keel. The cup is installed in the concave cavity, and the rigid keel is forced into the stabilization channel.

5 Claims, 4 Drawing Sheets

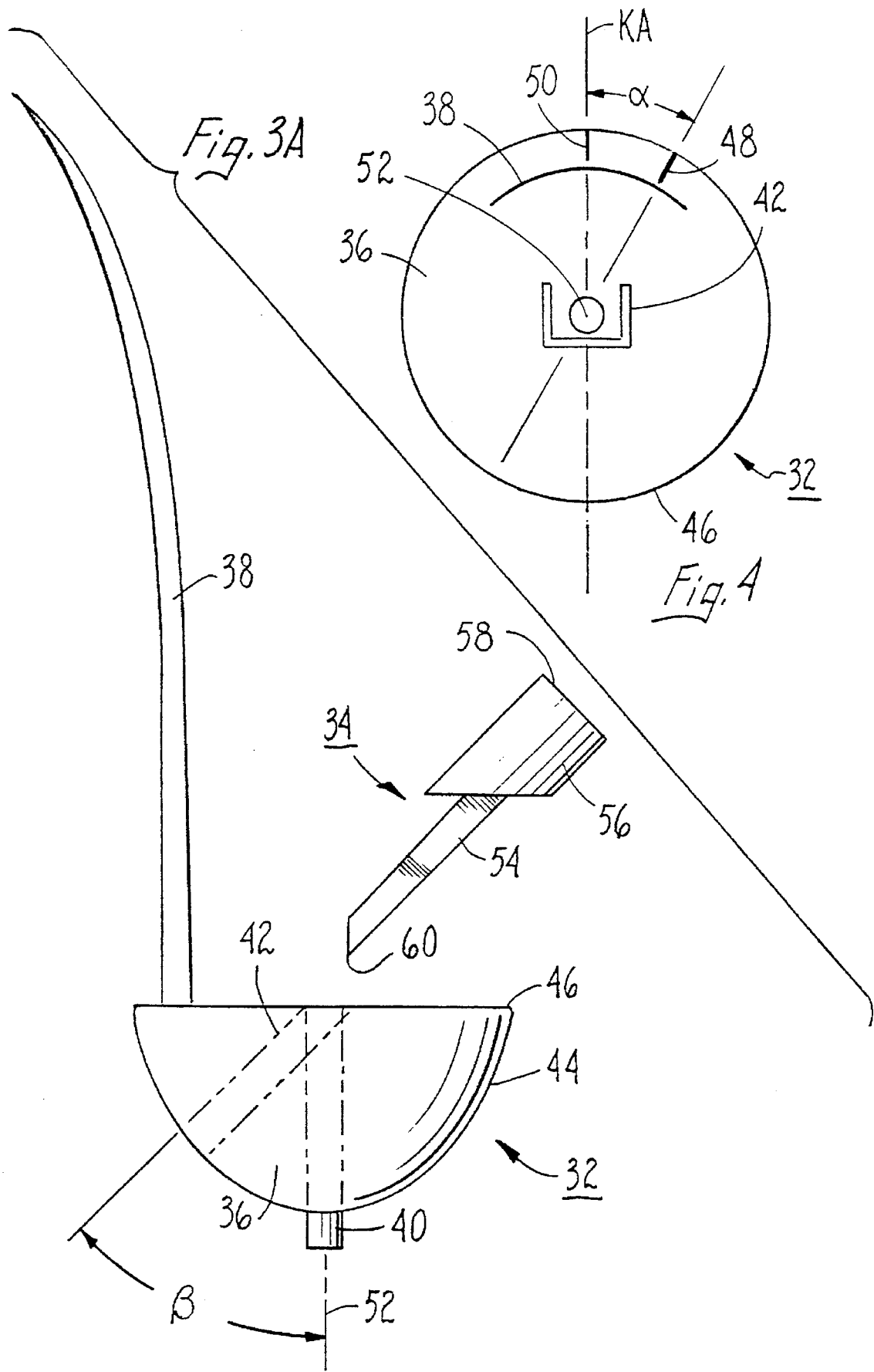

ACETABULAR CUP WITH KEEL

This is a continuation of application Ser. No. 08/232,689, filed Apr. 25, 1994 now abandoned.

FIELD OF INVENTION

This invention pertains generally to prosthetic devices. In particular, the present invention pertains to prosthetic devices used to rebuild the acetabulum in a pelvic bone.

BACKGROUND OF THE INVENTION

A number of techniques and devices have been developed for rebuilding or reconstruction of the acetabulum in a pelvis. It is the acetabulum into which the head of the femur fits to form the articulating hip joint. When undertaking a total or partial reconstruction of the hip joint, it is desirable to replicate the natural hip joint to the greatest degree possible. This means that the joint must be fully articulating, allowing a full range of normal movement of the femur relative to the pelvis. It is also necessary to ensure that any prosthesis used in the reconstruction will remain firmly in place after installation.

It is known to begin reconstruction of the acetabulum or socket by machining out the existing cavity to form a hemispherical cavity. A prosthetic cup is then installed into the new hemispherical cavity and usually cemented in place. The prosthetic cup will typically have an outer convex surface to conform to the hemispherical cavity and an inner concave surface to provide a new socket for the femoral head, or for a replacement femoral head. The prosthetic cup is held in place by the cement and by the natural process of ossification around the cup after installation.

These mechanisms result in varying degrees of success, depending upon the extent of deterioration of the existing pelvic bone and other factors. The cement can wear and loosen as a result of the repeated impact resulting from the normal use of the hip joint. In addition, further deterioration of the surrounding pelvic bone can severely reduce the available support for the prosthetic cup. Since the hip joint is often subjected to severe stress, the prosthetic cup can sometimes shift or even become dislodged, requiring further surgery and sometimes even causing further damage.

Therefore, it is an object of the present invention to provide a prosthetic cup for reconstruction of an acetabulum, which has a means of providing additional support from the pelvic bone. It is a further object of the present invention to provide an acetabular cup which receives much of its support from the inner portion of the pelvic structure relatively removed from the immediate acetabular cavity. It is yet another object of the present invention to provide a method of installing an acetabular cup which will result in support of the cup by an inner portion of the pelvic bone relatively removed from the acetabular cavity. Finally, it is an object of the present invention to provide an acetabular cup, and a method for its installation, which are easy and economical to construct and perform.

SUMMARY OF THE INVENTION

By way of example, the preferred embodiment of the present invention is a substantially ellipsoidal, non-spheroidal cup having a solid body and a rigid longitudinal keel. The body of the cup is formed from a relatively rigid solid material, such as metal, a ceramic, or high density polyethylene. The body has an outer convex ellipsoidal surface and an inner concave spheroidal surface or depression. The convex surface is a portion of the surface of a non-spherical ellipsoid, with the central axis of the convex surface being the major axis of the ellipsoid. Annular grooves are formed in the convex surface, oriented orthogonal to the major axis of the ellipsoid. The convex surface is formed to fit closely into an ellipsoidal cavity which will be machined into the pelvic bone. The concave surface or depression in the cup serves as the new acetabulum into which the femoral head will fit. The face of the cup surrounding the concave surface, between the concave surface and the rim of the cup, is exposed and acts as a replacement exterior surface of the pelvis, essentially matching the shape of the surrounding pelvic bone.

A rigid longitudinal keel extends from the convex surface of the cup, at an angle from the major axis of the ellipsoid. The keel can be constructed from any of a variety of rigid materials, including various metals. The keel has a flat tab portion and two longitudinal ribs extending orthogonally from the flat tab, to form a U-shaped cross section. Such a structure is designed to provide stiffness in all directions. The keel serves to anchor the acetabular cup in a region of the pelvic bone near the original acetabulum, thereby increasing the stability of the cup installation.

The method of installing the cup begins by drilling a pilot hole into the pelvic bone, essentially at the center of the original acetabular cavity. The alignment of the pilot hole is accomplished by use of a drill fixture which is aligned with a plurality of anatomical references on the pelvis. Using the pilot hole as a guide, the pelvic structure is machined away by known means to form a non-spherical ellipsoidal cavity larger than the original acetabulum. This can be performed by using an ellipsoidal cutter designed for the purpose, or using other known implements.

A guide fixture is then placed in the ellipsoidal cavity, with its central axis aligned with the pilot hole. The guide fixture is angularly aligned with the pelvis by means of a reference marker or line on the guide fixture, passing through the axis of the fixture. This reference marker is positioned to align generally with one or more anatomical references on the pelvis. This properly positions the guide fixture. A guide slot is formed in the guide fixture, having a cross section in the shape of a U-shaped channel matching the U-shaped cross section of the keel of the acetabular cup. The guide slot is angularly oriented about the axis of the guide fixture so that, when the guide fixture is properly positioned, the guide slot is aimed at the center, or heaviest part, of the body of the ilium. The guide slot does not extend radially from the axis of the guide fixture, instead forming an angle with the axis which is slightly less than the angle on the keel.

A trocar having a blade with a U-shaped cross section is driven through the guide slot into the body of the ilium to form a U-shaped cup stabilization channel in the ilium. The trocar and the guide fixture are then withdrawn from the ellipsoidal hemispherical cavity in the pelvis. Finally, the acetabular cup is placed in the ellipsoidal cavity, with the keel being forced into the cup stabilization channel, to create a force fit between the keel and the surrounding bone.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 3A is an elevation view of the guide fixture and trocar used in performing the method of the present invention;

FIG. 4 is a plan view of the guide fixture shown in FIG. 3A;

DESCRIPTION OF PREFERRED EMBODIMENTS

Figure 1:
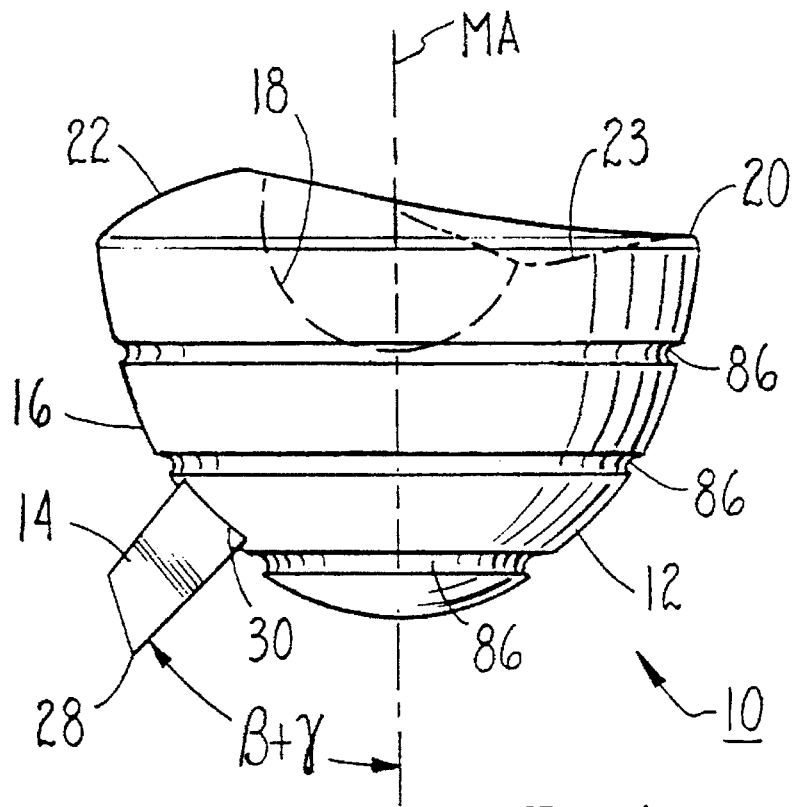
FIG. 1 is an elevation view of an acetabular cup of the present invention.
Figure 2:
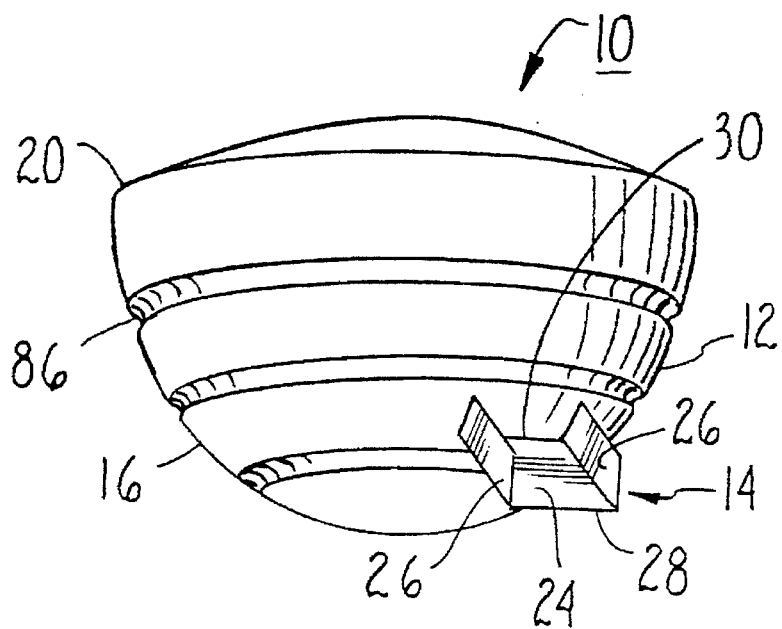
FIG. 2 is a perspective view of the acetabular cup shown in FIG. 1.

As shown in FIGS. 1 and 2, the preferred embodiment of the cup of the present invention is a substantially ellipsoidal cup 10 having a solid body 12 and a rigid longitudinal keel 14. The body 12 of the cup 10 is formed from a relatively rigid solid material, such as metal, a ceramic, or high density polyethylene. The body 12 has an outer convex ellipsoidal surface 16 and an inner concave spheroidal surface or depression 18. The central axis of the convex surface 16 is the major axis MA of the ellipsoid. The convex surface 16 is ringed by a plurality of annular grooves 86 which are oriented orthogonal to the major axis MA. The concave surface 18 can be centered on the same axis, or it can be eccentric if required for the particular application. The convex surface 16 is formed to fit closely into an ellipsoidal cavity which will be machined into the pelvic bone. The concave surface or depression 18 in the cup 10 serves as the new acetabulum into which the femoral head will fit.

The rim 20 of the cup 10 will essentially align with the rim of the ellipsoidal cavity in the pelvic bone. The outer face 22, 23 of the cup 10 surrounding the concave surface 18, between the concave surface 18 and the rim 20 of the cup 10, is exposed and acts as a replacement exterior surface of the pelvis, essentially matching the shape of the surrounding pelvic bone. The superior outer face 22 of the cup 10 can extend beyond the rim 20, and the inferior outer face 23 can lie below the rim 20, to conform to surrounding pelvic structure and to allow proper articulation of the hip joint. The superior outer face 22 will generally align with the ilium, and the inferior outer face 23 will generally align with the acetabular notch.

A rigid longitudinal keel 14 extends from the convex surface 16 of the cup 10 at an angle from the major axis MA. The angle is designated $\beta+\gamma$, where $\beta$ is equal to approximately forty-five degrees (45°), and $\gamma$ is equal to between one and three degrees (1° to 3°). The keel 14 can extend at other angles if required for the particular application, but the relationship between the angle of the keel and a cup stabilization channel, to be explained later, must always be maintained. The keel 14 can be constructed from any of a variety of rigid materials, including various metals. The keel 14 is attached to the cup 10 at its base 30, with its outer end 28 extending from the convex surface 16. The keel 14 has a flat tab portion 24 and two longitudinal ribs 26 extending orthogonally from the flat tab 24, to form a U-shaped cross section. Such a structure is designed to provide stiffness in all directions. Variations of this configuration can be used, as long as they incorporate rigid members joined at an angle to promote rigidity. The keel 14 serves to anchor the acetabular cup 10 in pelvic bone which is alongside, but sturdier than, the original acetabulum, thereby increasing the stability of the cup installation.

OPERATION

Figure 3B:
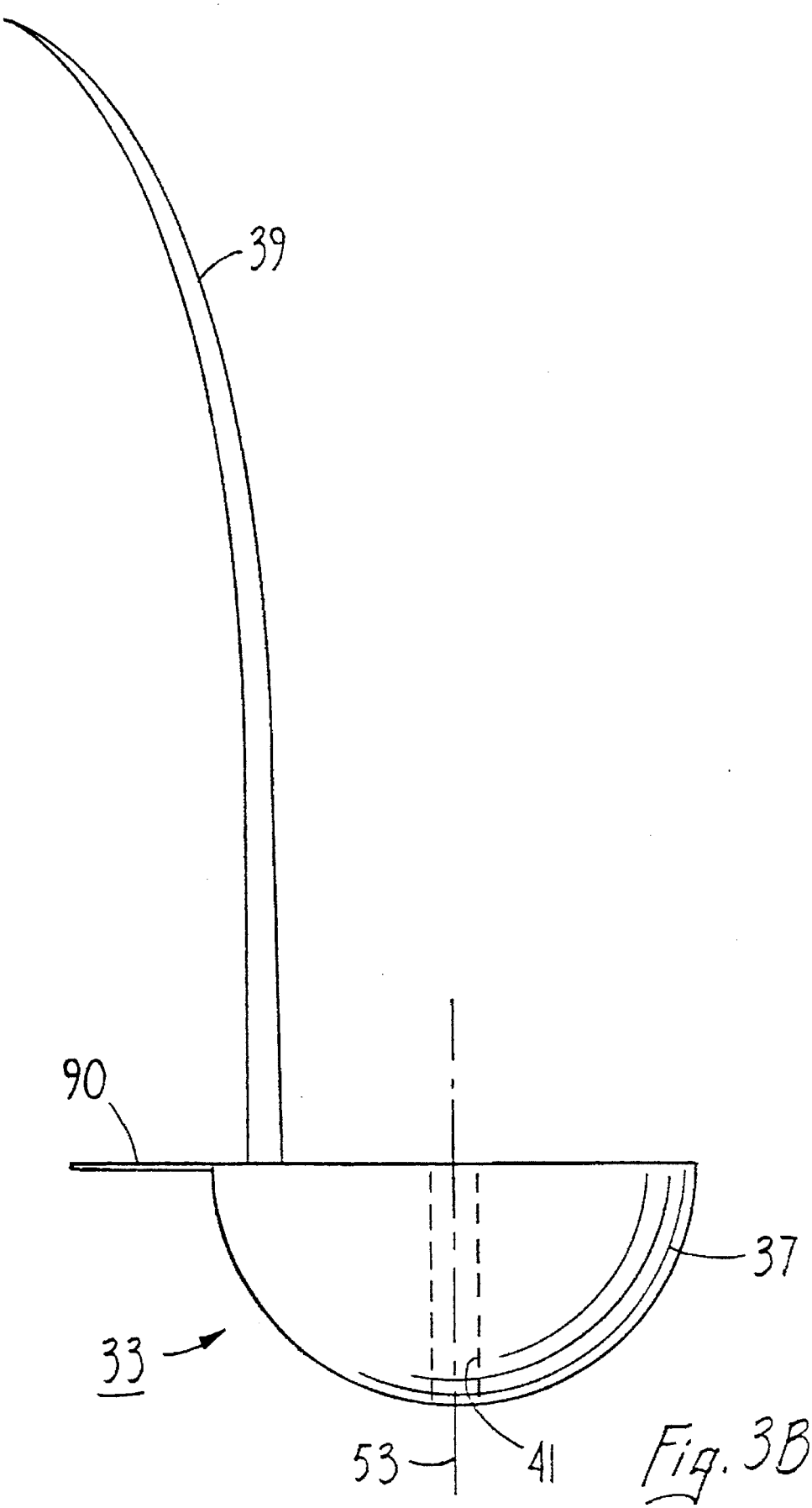
FIG. 3B is an elevation view of the drill fixture used in performing the method of the present invention.

A drill fixture 33 and guide fixture 32 and a trocar 34, as shown in FIGS. 3A, 3B, and 4, are used in the method of installation of the acetabular cup 10 of the present invention. The fixture has two embodiments, one for use as a drill fixture 33, and one for use as a guide fixture 32. Each embodiment consists of a solid hemispherical body 36, 37 and a long curved handle 38, 39. A pilot pin 40 extends radially from the body 36 of the guide fixture 32, along the central axis 52 of the guide fixture 32. The drill fixture 33 is shaped essentially identically to the guide fixture 32, except that the body 37 of the drill fixture 33 has a through hole 41 along the axis 53, instead of the pilot pin 40. The drill fixture 33 also has a tab 90 extending from the edge of the body 37, to assist in aligning the drill fixture 33.

The body 36 of the guide fixture 32 is penetrated by a guide slot 42 which has a U-shaped cross section, or other appropriate cross section to match the cross section of the keel 14 on the acetabular cup 10. The guide slot 42 is oriented at the aforementioned angle $\beta$ from the axis 52 of the guide fixture 32, to ensure that the guide slot 42 forms an angle with the axis 52 which is 1° to 3° less than the angle of the keel 14 with respect to the axis of the acetabular cup 10. A guide slot indicator 50 is placed on the body 36 of the guide fixture 32 in angular alignment with the central axis KA of the guide slot 42. A reference marker 48 is placed on the body 36 at an angle $\alpha$ from the guide slot indicator 50. Angle $\alpha$ is approximately one-half the angle subtended by the body of the ilium, or approximately thirty degrees (30°).

The handle 38 attaches to the upper face of the body 36 and extends generally upwardly therefrom. The handle 36 is not shown in its entirety in FIG. 4, to allow other features to be seen. The handle 38 is a thin, curved, rigid structure which can be formed from sheet metal or plastic. The handle can be placed almost anywhere on the upper surface of the body 36, as long as it does not interfere with the movement or insertion of the trocar 34.

The trocar 34 consists of a rigid longitudinal blade 54 extending from a cylindrical base 56. The distal end 60 of the trocar blade 54 is relatively sharp and hard, in order to penetrate bone. The proximal end 58 of the trocar base 56 is relatively flat, to provide a hammering surface. The trocar blade 54 has a U-shaped cross section to match the cross sections of the guide slot 42 and the keel 14.

Figure 5:
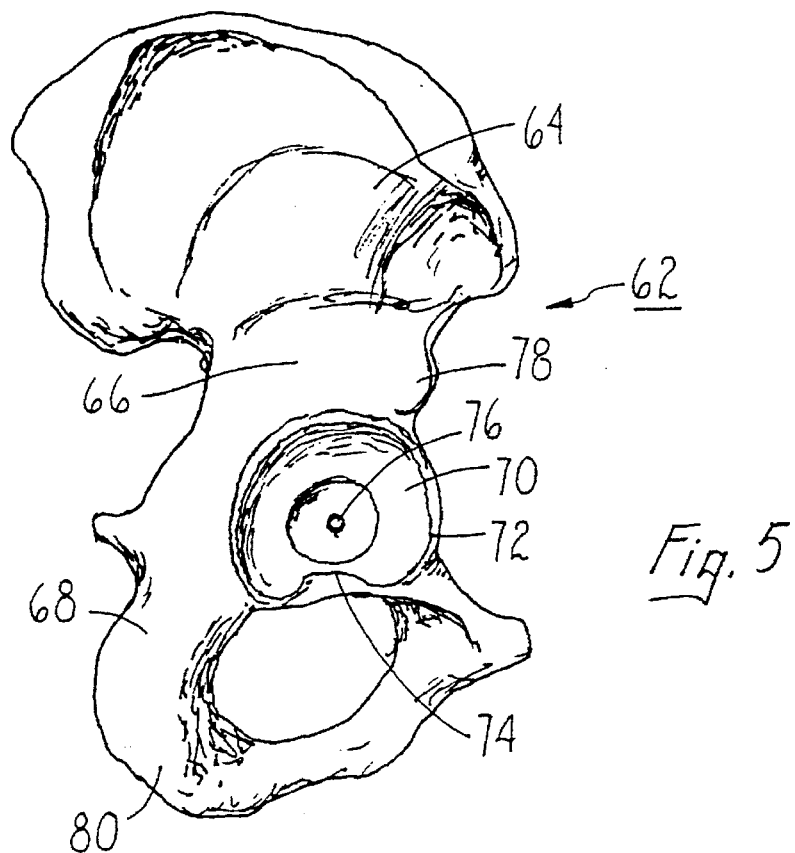
FIG. 5 is a lateral view of the right side of a pelvis, showing the pertinent features.
Figure 6:
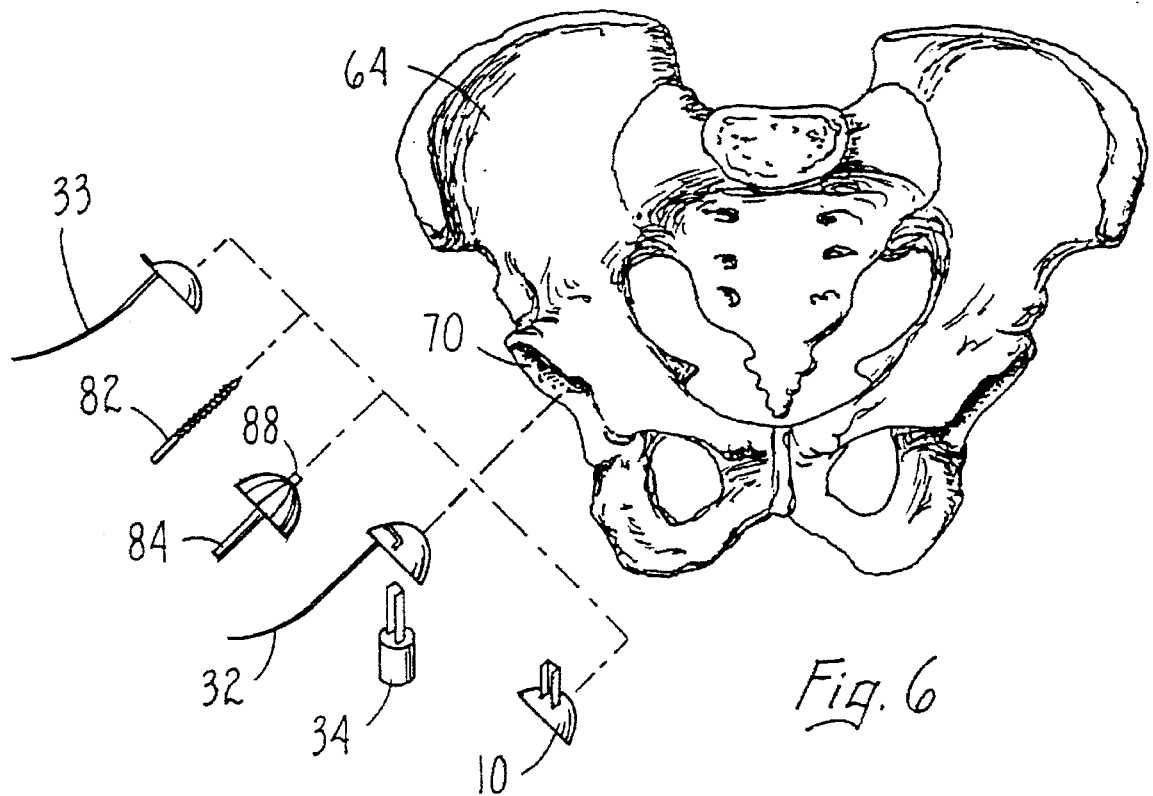
FIG. 6 is an anterior view of a pelvis, showing the relative orientation of the instruments used in performing the method of the present invention.

Referring now to FIGS. 5 and 6, a pelvic bone 62 is shown, having an ilial wing 64, body of the ilium 66, ischium 68, and acetabulum 70 as shown. The bony margin 72 of the acetabulum 70 can be deteriorated beyond the condition shown. The method of installing the cup 10 begins by using a pilot drill 82 to drill a pilot hole 76 into the pelvic bone 62, essentially at the center of the original acetabular cavity 70. The alignment of the pilot hole 76 is accomplished with reference to known anatomical reference points, and according to the judgement of the physician to result in eventual proper alignment of the prosthetic cup 10. The drill fixture 33 is placed in the acetabulum and reference marks are aligned with the known anatomical reference points as follows: The first mark 78 is located on the posterior superior iliac spine, and a second Bowie Mark 79 is located on the acetabular rim at the end of the fovia centralis. The pilot hole 76 is then drilled using the pilot drill 82.

Using the pilot hole 76 as a guide, the pelvic structure is machined away by known means to form an ellipsoidal cavity larger than the original lunate surface of the acetabulum 70. This can be performed by using an ellipsoidal cutter 84 having as its central axis the major ellipsoidal axis. A spring loaded pilot pin 88 is mounted on the central axis of the cutter 84. As the ellipsoidal cavity is machined, the spring loaded pilot pin 88 retracts partially into the cutter 84, to avoid breaking through the ilium.

The guide fixture 32 is then placed in the ellipsoidal cavity, with its axis 52 aligned with the pilot hole 76, and with the pilot pin 40 in the pilot hole 76. The guide fixture outer rim 46 will generally align with the bony margin 72. The guide fixture 32 is angularly aligned in the ellipsoidal cavity by means of the reference marker or line 48 on the guide fixture 32, passing through the axis 52 of the guide fixture 32. One end of this reference marker 48 is positioned to align generally with the anterior inferior iliac spine 78 of the pelvis 62, and the other end of the reference marker 48 is positioned to align with the ischial tuberosity 80. This properly positions the guide fixture 32. The guide slot 42 formed in the guide fixture body 36 is now aimed at the center, or heaviest part, of the body of the ilium 66.

The trocar 34 is now driven through the guide slot 42 into the body of the ilium 66 to form a U-shaped cup stabilization channel (not shown) in the ilium. The trocar 34 and the guide fixture 32 are then withdrawn from the ellipsoidal cavity in the pelvis 62. Finally, the acetabular cup 10 is inserted into the ellipsoidal cavity over the acetabular notch 74, with the keel 14 being forced into the cup stabilization channel, and cemented in place.

While the particular Acetabular Cup With Keel as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A prosthetic cup for the reconstruction of the acetabulum, comprising:

a cup-shaped body positionable on said acetabulum in a predetermined orientation, said body having a prolate ellipsoidal convex surface formed on a first side of said body and having a central axis extending through a central point of said convex surface, the ellipsoidal convex surface having a major ellipsoidal axis and a minor ellipsoidal axis, the major ellipsoidal axis comprising said central axis and extending through the central point of said surface, the major axis being longer than the minor axis;

a plurality of annular grooves formed on said convex surface, said grooves being oriented orthogonal to said major ellipsoidal axis;

a substantially spheroidal concave surface formed on a second side of said body, said major ellipsoidal axis extending through the second side of said body; and a rigid stabilization keel attached to said body and projecting outwardly from said convex surface.

2. A cup as claimed in claim 1, wherein said cup-shaped body is a one-piece member and said spheroidal concave surface has a central axis extending at an acute angle to said major ellipsoidal axis.

3. A cup as claimed in claim 1, wherein said ellipsoidal convex surface has a peripheral rim for alignment with an ellipsoidal cavity in a pelvic bone and said rigid keel comprises a flat longitudinal tab having a base attached to said convex surface at a location spaced from said peripheral rim.

4. A cup as claimed in claim 3, wherein said rigid keel further comprises at least one flat longitudinal rib formed on said tab and extending orthogonally therefrom.

5. A cup as claimed in claim 1, wherein said rigid keel comprises a longitudinal tongue having a U-shaped cross-section, said convex surface having a peripheral rim for alignment with an ellipsoidal cavity in a pelvic bone, and said tongue having a base secured to said convex surface at a location spaced from said peripheral rim and positioned closer to said central point of said convex surface than said rim.

* * * * *